United States Patent
Ling et al.

(10) Patent No.: US 6,808,490 B1
(45) Date of Patent: Oct. 26, 2004

(54) PENILE PROSTHESIS WITH IMPROVED TUBING JUNCTION

(75) Inventors: Jeremy J. Ling, St. Paul, MN (US); Randy L. Morningstar, Brooklyn Park, MN (US); Stephanie A. George, St. Louis Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/423,348

(22) Filed: Apr. 25, 2003

(51) Int. Cl.[7] .................................................. A61F 5/00
(52) U.S. Cl. ........................................................ 600/40
(58) Field of Search ...................... 600/29–31, 38–41; 128/897, 899, DIG. 25; 623/11.11, 23.64, 23.67, 66.1

(56) References Cited

U.S. PATENT DOCUMENTS

| | | | | |
|---|---|---|---|---|
| 4,718,410 A | * | 1/1988 | Hakky | 600/40 |
| 5,062,417 A | * | 11/1991 | Cowen | 600/40 |
| 5,250,020 A | * | 10/1993 | Bley | 600/40 |

* cited by examiner

*Primary Examiner*—Samuel G. Gilbert

(57) ABSTRACT

The present disclosure relates to penile implants that are easier to implant and reduce trauma because they provide for a smaller effective width during implantation, after implantation, or both. The present disclosure also provides for a shorter tubing junction while reducing effective width, further reducing trauma to the body. In a first aspect, the penile implant includes a tubing junction that is smaller in effective diameter while implanted in the body. The penile implant includes an axially extending cylinder having an inflation chamber and a rear tip. The cylinder also includes a tubing junction disposed between the inflation chamber and rear tip and extending from the cylinder. The tubing junction includes a bore in fluid communication with the inflation chamber. In one example, this bore is in the strain relief of the tubing junction. The bore is configured to include a compound curve. In another aspect, the penile implant includes a tubing junction that can assume a smaller effective diameter while being implanted into the body. The surgeon is able to press the tubing against the cylinder than the related art to reduce the effective area of the penile implant. This penile implant includes a cylinder having an inflation chamber and a rear tip. A tubing junction is disposed between the inflation chamber and the rear tip. The tubing junction includes a strain relief that extends from the cylinder and forms an acute area proximate the intersection of the cylinder and the strain relief. The acute area includes a keyhole.

6 Claims, 3 Drawing Sheets

PENILE PROSTHESIS WITH IMPROVED TUBING JUNCTION

BACKGROUND

The present disclosure relates to medical devices used in implant surgery. More specifically, the present disclosure relates to an inflatable penile prosthesis, or penile implant.

The study of impotence has recently become center stage in the field of medicine. In the early 1970's, the conventional view was that ninety percent of impotence cases were psychologically based, whereas only ten percent of the cases were caused by a physical condition. Today, doctors and scientists understand that the overwhelming majority of cases are caused by a physical condition. Accordingly, more and more resources are poured into the study of and treatment for impotence. According to a recent study, fifty-two percent of men between the ages of forty and seventy self-reported that they suffer from some type of erectile dysfunction. Another study estimated that over thirty million American men and their partners suffer from erectile dysfunction.

Advertisements for pharmaceutical treatments for impotence have become ubiquitous, and include endorsements from celebrities that suffer from erectile dysfunction. More and more men and their partners now are seeking treatment for impotence. In the recent past, it was estimated that only one in twenty sufferers of erectile dysfunction sought treatment from their doctors. Pharmaceutical treatments are successful for only a subset of impotence sufferers. More invasive treatments are necessary for many men. These treatments include injection therapy, vacuum devices and penile prosthesis.

For many impotence sufferers, the penile implant is the only solution to restore a happy and healthy sex life. The penile implant has been used for decades and provides a selected and reliable erection. The penile implant often includes a pair of cylinders. In some instances, these cylinders are inflatable, and are connected to a fluid-filled reservoir with a pump and valve assembly. The two cylinders are normally implanted into the corpus cavernosae of the patient's penis and the reservoir is typically implanted into the patient's abdomen. The pump assembly is implanted in the scrotum. During use, the patient actuates the pump and fluid is transferred from the reservoir through the pump and into the cylinders. This results in the inflation of the cylinders and produces rigidity for a normal erection. Then, when the patient desires to deflate the cylinders, a valve assembly within the pump is actuated in a manner such that the fluid in the cylinders is released back into the reservoir. This deflation returns the penis to a flaccid state.

A type of inflatable penile implant includes a cylinder having an inflation chamber side that is disposed within the penis (distal corpus cavernosae) and rear tip side that is disposed within the body (proximal corpus cavernosae). The penile implant includes a remote pump assembly that is connected via tubing to the cylinder. The tubing is connected to the cylinder at a tubing junction. Typically, this tubing junction is located near the interface between the inflation chamber and the rear tip. The tubing junction includes a strain relief that extends from the cylinder like a branch from a tree trunk. The tubing is inserted into the strain relief. In prior art examples, such as those in U.S. Pat. Nos. 4,651,721 and 5,167,611, among others, show a straight bore extending through the strain relief and into the inflation chamber. Fluid is transferred from the pump assembly, through the tubing, and into the inflation chamber.

The penile implant is an invasive treatment and requires a delicate and painful implant surgery to install. To reach the corpus cavernosum and implant the cylinders, the surgeon will first make an incision at the base of the penis, such as where it meets the scrotum. The patient is prepared for the cylinder after the surgeon has dilated each corpus cavernosum to create space for the cylinders. The distal end of the cylinder, i.e., the inflation chamber, is inserted into the corpus cavernosum. The proximal end of the cylinder, i.e., the rear tip and tubing junction, is inserted back into the body toward the pubic bone.

The tubing junction, and particularly the strain relief, increases the effective width, or effective diameter, of the cylinder. This increased width can create problems for both the surgeon and the patient during surgery. Some physicians have difficulty dilating the proximal corporal body sufficiently to accept the proximal end of the cylinder. And the added effective diameter of the tubing junction sometimes requires that the surgeon force the device through pelvic tissue, such as severe fibrotic tissue in some patients. This can make proper insertion and placement more difficult than if the cylinder were easily inserted, and can require further cutting and trauma. Further, the added effective width causes an increase in trauma to what is otherwise a sensitive area for the patient, which can require longer healing times.

SUMMARY

The present disclosure relates to penile implants that are easier to implant and reduce trauma because they provide for a smaller effective width during implantation, after implantation, or both. The present disclosure also provides for a shorter tubing junction while reducing effective width, further reducing trauma to the body.

In the first aspect, the present disclosure relates to a penile implant that includes a tubing junction that is smaller in effective diameter while implanted in the body. A penile implant includes an axially extending cylinder having an inflation chamber and a rear tip. The cylinder also includes a tubing junction disposed between the inflation chamber and rear tip and extending from the cylinder. The tubing junction includes a bore in fluid communication with the inflation chamber. In one example, this bore is in the strain relief of the tubing junction. The bore is configured to include a compound curve. The compound curve in the bore permits the strain relief to lay flatter against the cylinder than a straight bore or even a bore with a "hairpin" curve.

In another aspect, the present disclosure relates to a penile implant that includes a tubing junction that can assume a smaller effective diameter while being implanted into the body. Specifically, the surgeon is able to press the tubing against the cylinder than the related art to reduce the effective area of the penile implant. This penile implant includes a cylinder having an inflation chamber and a rear tip. A tubing junction is disposed between the inflation chamber and the rear tip. The tubing junction includes a strain relief that extends from the cylinder and forms an acute area proximate the intersection of the cylinder and the strain relief. The acute area includes a keyhole. The keyhole permits the strain relief to lie closer to the cylinder without causing damage to the tubing, strain relief, or other parts of the prosthesis.

The present disclosure provides many advantages, among which two are listed here. These two aspects have been demonstrated to provide a cylinder having an advantageously smaller effective diameter during or after implantation than the related art. The tubing junction with a bore configured to include a curve having a compound angle provides noticeable advantages both during and after implantation. One example has been demonstrated to be at least approximately fifteen percent smaller in effective diameter over popular products of the related art. Additionally, the aspect with the keyhole has been demonstrated to permit the strain relief to lie flat, i.e., zero degrees, against the cylinder, during implantation of the device. Other advantages will become apparent to those skilled in the art.

DESCRIPTION

This disclosure relates to an improved penile implant. The disclosure, including the figures, describes the improved penile implant with reference to several illustrative examples. Other examples are contemplated and are mentioned below or are otherwise imaginable to someone skilled in the art. The scope of the invention is not limited to the few examples, i.e., the described embodiments of the invention. Rather, the scope of the invention is defined by reference to the appended claims. Changes can be made to the examples, including alternative designs not disclosed, and still be within the scope of the claims.

Figure 1:
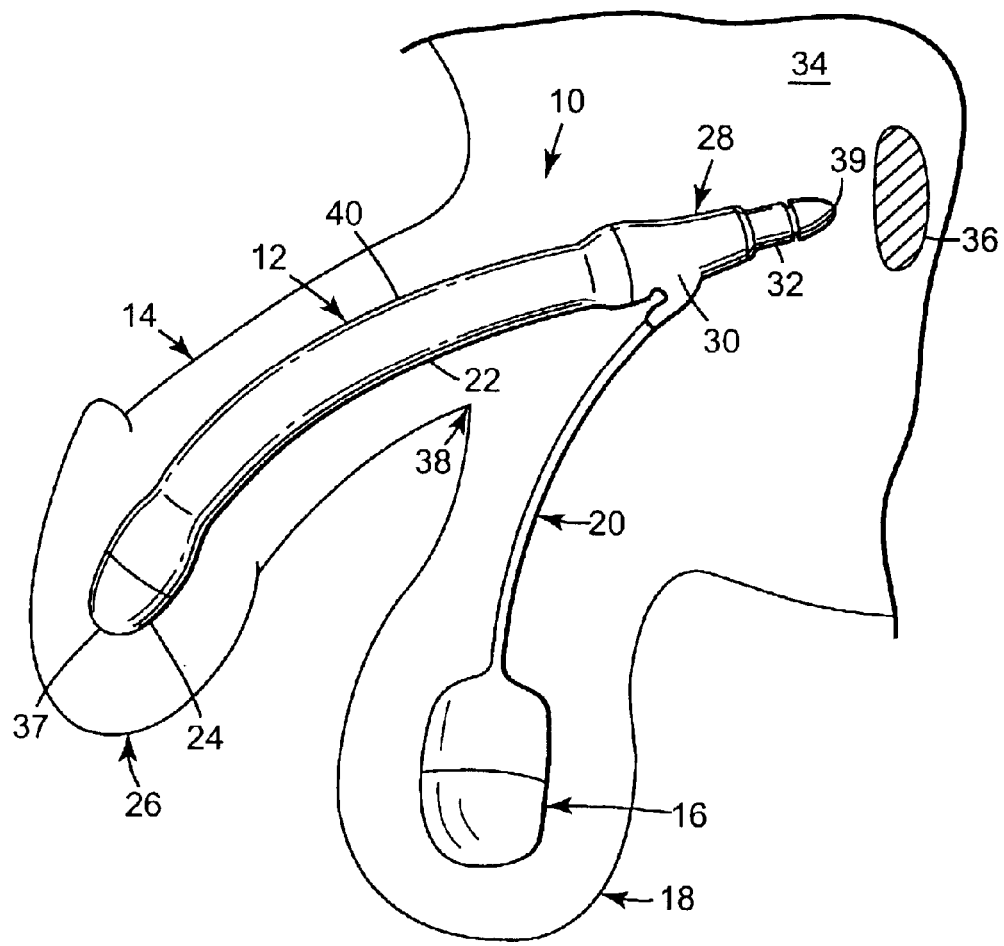
FIG. 1 is a schematic side view of a penile prosthesis implanted in a patient.

FIG. 1 is a schematic side view of a penile prosthesis 10 implanted in a patient. The prosthesis 10 includes a pair of cylinders, one of which is shown as cylinder 12, implanted in a penis 14. The prosthesis can also include a pump 16, often implanted into the patient's scrotum 18. The tubing 20 attaches the pump 16 to the cylinders such that the pump 16 is in fluid communication with the cylinder 12. In still an alternative example, the pump 16 can be in fluid communication with a fluid reservoir (not shown) that is often implanted into the patient's abdomen. The prosthesis including cylinders, pump, and fluid reservoir is referred to as a three-piece device. In the present example, the prosthesis 10 includes a pair of cylinders 12 and a pump 16 and is known as a two-piece device. The disclosure is directed to devices including a tubing attached to the cylinders, and thus includes both two and three-piece devices.

The cylinder 12 includes an inflation chamber 22 that is disposed within the penis 14. The distal end 24 of the cylinder 12 is disposed within the crown 26 portion of the penis 14. The cylinder also includes a proximal end 28 that often includes the tubing junction 30, i.e., the structural portion of the cylinder 12 connected to the tubing 20, and the rear tip 32 of the cylinder 12. The proximal end 28 is typically implanted into the patient's pubic region 34 with the rear tip 32 proximate the pubic bone 36.

Figure 2:
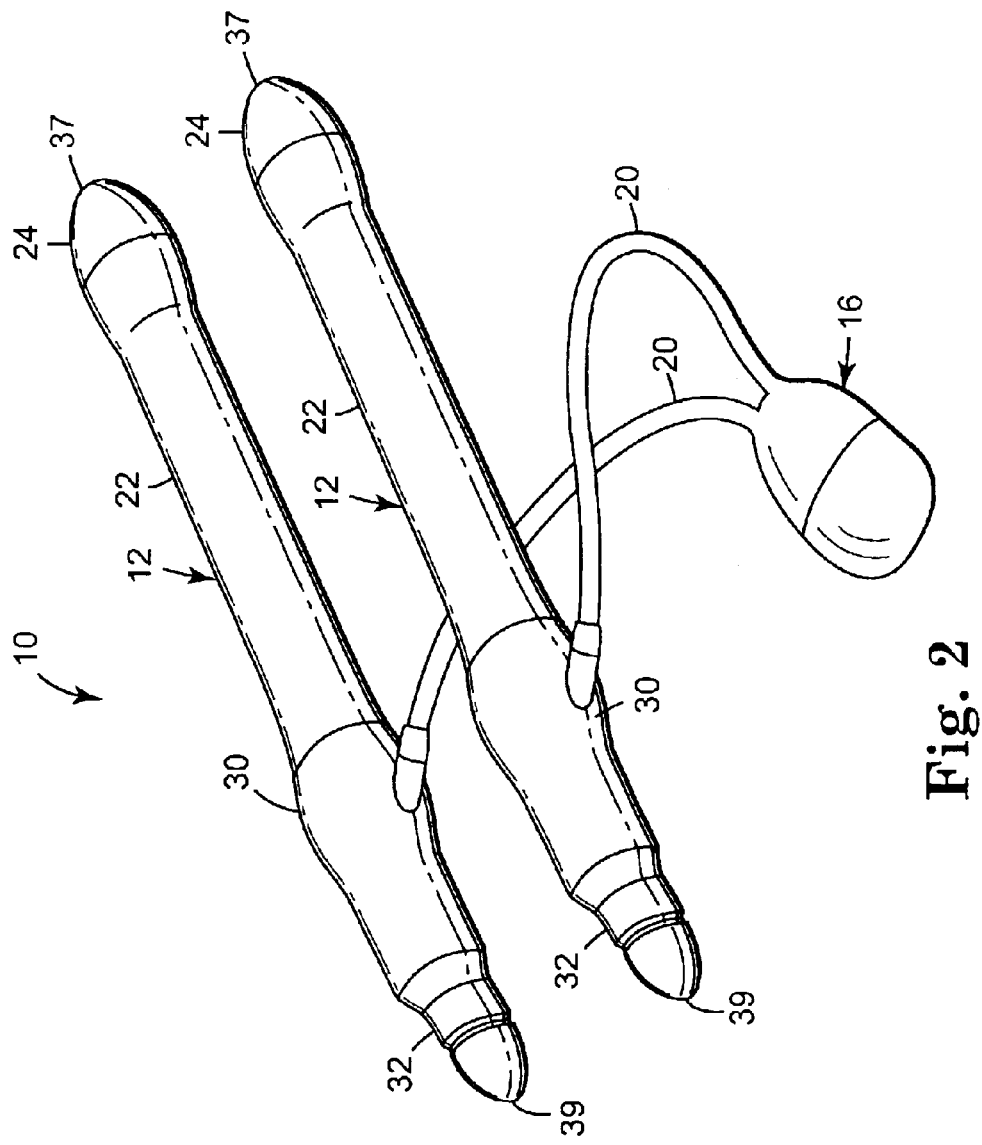
FIG. 2 is a perspective view of the penile prosthesis of FIG. 1.

The prosthesis 10 is shown by itself in FIG. 2. The prosthesis includes a pair of cylinders 12 connected by tubing 20 to a pump 16. Like parts of each cylinder are given the same reference number. Accordingly, the prosthesis 10 is a two-piece device. The prosthesis includes two cylinders 12, one for each side of the penis. Each cylinder includes a distal end 24 having a distal tip 37, an inflation chamber 22 and a proximal end 28 including a tubing junction 30, a rear tip 32 and a rear end 39. The pump 16 serves to inflate both cylinders 12. In the case of a three-piece device, typically one fluid reservoir is connected in fluid communication with the pump.

In order to implant the cylinders 12, the surgeon first prepares the patient. The surgeon often makes an incision in the penoscrotal region 38, i.e., where the base of the penis 14 meets with the top of the scrotum 18. From the penoscrotal incision, the surgeon will dilate the patient's corpus cavernosae 40 to prepare the patient to receive the cylinders 12. The corpus cavernosum is one of two parallel columns of erectile tissue forming the dorsal part of the body of the penis 14, i.e., two slender columns that extend substantially the length of the penis. The surgeon will also dilate two regions of the pubic area (proximal corpora cavernosae) to prepare the patient to receive the proximal ends 28. The surgeon will measure the length of the proximal and distal corpora cavernosae from the incision and the dilated region of the pubic area to determine an appropriate size of the cylinders 12 to implant.

After the patient is prepared, the prosthesis 10 is implanted into the patient. The distal tip 37 of each cylinder often is attached to a suture. The other end of the suture is often then attached to a Keith needle. The Keith needle is inserted into the incision and into the dilated corpus cavernosum. The Keith needle is then forced through the crown of the penis. The surgeon tugs on the suture to pull the cylinder into the corpus cavernosum. This is done for each cylinder. Once the inflation chamber 22 is in place, the surgeon removes the suture from the distal end 37. The surgeon then inserts the proximal end 28. The surgeon inserts the rear ends 39 into the incision and forces the proximal ends 28 toward the pubic bone 36 until the cylinders are in place.

Figure 3:
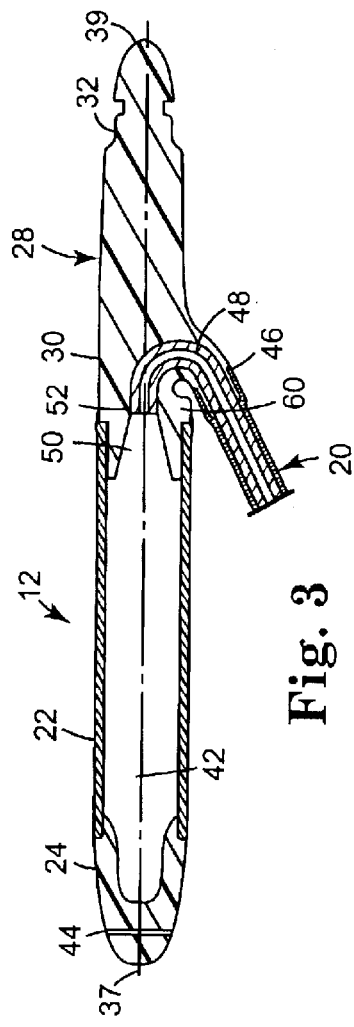
FIG. 3 is a side sectioned view of a portion of the penile implant of FIG. 2.

FIG. 3 shows a side sectioned view of one of the cylinders 12 and a portion of its associated tubing 20. The cylinder 12 includes an axis 42. The distal end 24 and proximal end 28 are disposed along the axis 42.

The distal end 24 forms part of the inflation chamber 22. The distal end 24 is generally solid but can include a hole 44 that is adapted to receive the suture described above. In the example, the distal end 24 is constructed from a silicone rubber or silicone elastomer. The inflation chamber 22 in the example includes a multilayer tube. The example includes three layers. The innermost layer is an extruded silicone elastomer, the middle layer is a distensible fabric such as a polyester and spandex blend, and the outer layer is also an extruded silicone. The layers can include a coating such as parylene. Parylene coating is a medical grade polymer intended to reduce friction-based wear occurrences. Parylene can be applied to the layers as is known in the art.

The proximal end 28 includes the rear tip 32 and the tubing junction 30. In the example, the rear tip 32 is solid and formed from a silicone rubber or silicone elastomer. The rear tip can also include barium sulfate, so that it can be easily visible in an X-Ray of the region. The barium sulfate can also be added to other parts of the prosthesis for the same purpose. Other radio-opaque substances or markers can be used, such as aluminum oxide, iridium, or others. The section of the rear tip 32 near the rear end 39 can be adapted to receive a rear tip extender as is known in the art. In one example, the approximate length of the rear tip 32, from the tubing junction 30 to the rear end 39, is three centimeters, which has been determined to be an advantageous length. In cases where this length is not long enough, rear tip extenders are used for the proper fit.

The tubing junction 30 is disposed between the inflation chamber 22 and the rear tip 32. The tubing junction includes a strain relief 46 branching from the axially extending cylinder. The strain relief 46 includes a bore 48 extending into the axially extending cylinder into a flared opening 50 in fluid communication with the inflation chamber 22. In the example, a silicone rubber tube, or input tubing 52 portion of tubing 20, is disposed within the bore 48 up to the flared opening 50. The tubing 52 is attached to the strain relief 46 and is commonly known as kink resistant tubing, which can include a nylon suture filament to reduce the chance of the tube kinking after implant. The strain relief is generally more rigid than the tubing 20, and prevents the tubing 20 from over flexing against the tubing junction 32, which can damage the tubing or cause kinking and occluding flow.

Figure 4:
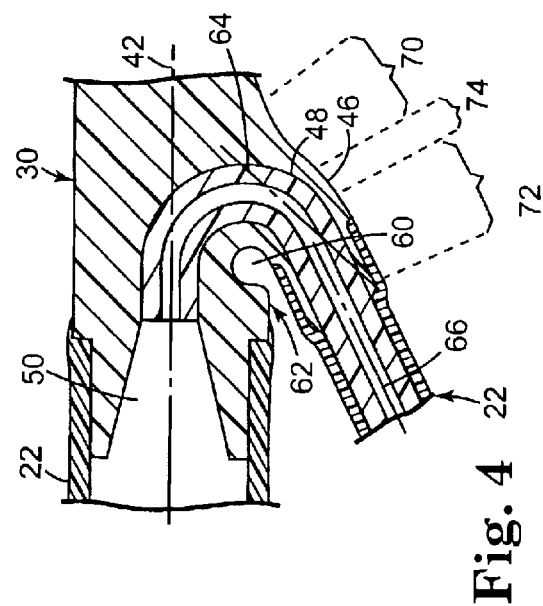
FIG. 4 is an enlarged side sectioned view of the portion of the penile implant of FIG. 3.

FIG. 4 is an enlarged view of the tubing junction 30 shown in FIG. 3. The tubing junction 30 includes a keyhole 60 formed in the acute area 62, i.e., the area between the strain relief and the axially extending cylinder. The keyhole 60 in the example is a circular cutout of material forming indents in the axially extending cylinder 12 and the strain relief 46. Indents in the cylinder 12, strain relief 46, or both, provide the ability for the strain relief 46 to be flexed against the cylinder 12 in a smaller effective diameter than without the keyhole. The surgeon squeezes the strain relief and tubing against the cylinder, and the cylinder will have a smaller effective diameter than without the keyhole, so that the proximal end can be implanted easier than before or into a less dilated region of the body.

The keyhole 60 in the example is disposed in the acute area directly where the strain relief joins the cylinder. The cylinder proximate the acute area does not continue with a generally smooth profile into the strain relief, but instead includes an indent causing a widening of the acute area. Similarly, in the example, the strain relief proximate the acute area does not include a smooth profile into the cylinder, but instead also includes an indent causing a further widening of the acute area. This widening of the acute area permits the strain relief to fold against the cylinder with a smaller effective diameter than without the keyhole.

The keyhole 60 is subject to many variations. For example, the keyhole 60 need not be circular, but could be oval or any other suitable shape. The keyhole preferably includes indents in both the strain relief 46 and cylinder 12 in the acute area 62. Indents, however, could be provided in either the strain relief or the cylinder.

The bore 48 in the strain relief 46 follows a curve having a compound angle (or "compound curve" as may be used here) that also provides for a lower effective diameter. In contrast to the keyhole, the compound angle provides the cylinder with a lower effective diameter when the strain relief 46 is not urged against the cylinder. Accordingly, a prosthesis with both a keyhole and a compound curve in the strain relief provides the surgeon with an ease of insertion and the patient with a less invasive prosthesis. The compound curve does not provide impediments to inflating or deflating the inflation chamber.

The compound curve in the example has at least one bend in the strain relief bore 48. One way to describe the curve having a compound angle is that the path of the bore in the strain relief has at least two angles with respect to the axis 42 of the cylinder. Another way to describe the compound curve is that the bore follows more than one radius of curvature in the strain relief. In the example, the bore initially extends from the cylinder, at region 70, at an angle of 43 degrees between the axis 64 of region 70 from the axis 42 of the cylinder. At region 72, the angle between the axis 66 of region 72 and the axis 42 of the cylinder is only 22 degrees. In other words, the radius of curvature of the bore at region 70 is less than the radius of curvature of region 72.

In the example, the bore follows a smooth curvilinear path. The changes in the radius of curvature or angle from the axis are subtle and not abrupt. The acute angles formed in region 70 and 72 are separated by transition region 74. In some examples, the compound curve need not include transition region 74, and the change in angles is abrupt. For the purposes of this disclosure, such abrupt changes are also considered compound curves. The examples show strain relief having two angles or radii of curvature. More angles or radii of curvature are possible. The two angle or radii construction having acute angles of 43 and 22 degrees has been determined to optimize the need for a low profile or effective diameter of the cylinder and for manufacturing efficiency.

The application of a compound curve strain relief also permits greater flexibility in design of the prosthesis. The bore configured to include a compound curve permits a low profile and a shorter tubing junction length, as measured along the axis of the cylinder. With a shorter length of tubing junction, the length of the rear tip 32 and inflation chamber 22 can be optimized, as understood by designers. For example, a shorter tubing junction 30 can permit a longer rear tip, and the surgeon will not need to dilate the body to make room for the strain relief.

The present invention has now been described with reference to several embodiments. The foregoing detailed description and examples have been given for clarity of understanding only. Those skilled in the art will recognize that many changes can be made in the described embodiments without departing from the scope and spirit of the invention. Thus, the scope of the present invention should not be limited to the exact details and structures described herein, but rather by the appended claims and equivalents.

What is claimed is:

1. A penile prosthesis, comprising a pair of cylinders each having an inflation chamber and a rear tip;

a tubing junction disposed between the inflation chamber and the rear tip of each of the cylinders, the tubing junction including a strain relief extending from each of the cylinders and forming an acute area proximate the intersection of each of the cylinders and the strain relief;

wherein the acute area includes a keyhole.

2. The penile prosthesis of claim 1 wherein the keyhole includes an indent in the cylinder.

3. The penile prosthesis of claim 2 wherein the keyhole includes an indent in the tubing junction.

4. The penile prosthesis of claim 2 wherein the keyhole further includes an indent in the strain relief.

5. The penile prosthesis of claim 1 wherein the keyhole is circular.

6. A penile implant, comprising:

a cylinder having an inflation chamber and a rear tip, the cylinder having an axis;

a tubing junction disposed between the inflation chamber and the rear tip and extending from the cylinder, the tubing junction having a strain relief including a bore in fluid communication with the inflation chamber;

wherein the bore is configured to include a compound curve;

wherein the strain relief intersects the cylinder at an acute area; and wherein the acute area includes a keyhole.

* * * * *